(12) United States Patent
Komeda et al.

(10) Patent No.: US 6,423,510 B1
(45) Date of Patent: Jul. 23, 2002

(54) *CANDIDA BOIDINI* DIHYDROXYACETONE SYNTHASE PROMOTER

(75) Inventors: Toshihiro Komeda; Keiji Kondo, both of Kanagawa; Nobuo Kato; Yasuyoshi Sakai, both of Kyoto, all of (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/622,540

(22) PCT Filed: Feb. 18, 1999

(86) PCT No.: PCT/JP99/00729

§ 371 (c)(1),
(2), (4) Date: Aug. 18, 2000

(87) PCT Pub. No.: WO99/42572

PCT Pub. Date: Aug. 26, 1999

(30) Foreign Application Priority Data

Feb. 19, 1998 (JP) ............................................. 10-037263

(51) Int. Cl.[7] ......................... C12P 21/06; C12N 15/00; C12N 5/06; C07H 21/02
(52) U.S. Cl. .............. 435/69.1; 435/320.1; 435/354.22; 536/24.1
(58) Field of Search ...................... 536/24.1; 435/320.1, 435/69.1, 252.3, 254.22

(56) References Cited

FOREIGN PATENT DOCUMENTS

| | | |
|---|---|---|
| EP | 0 558 024 | 2/1993 |
| WO | 97/10345 | 3/1997 |

OTHER PUBLICATIONS

Haywood G. et al, Microbial oxidation of amines. Distribution, purification and properties of two primary–amine oxidases from the yeast *Candida boidini* grown on amines as sole nitrogen source, Biochem., J. 1981, 199, 187–201.*

Allen S. J. et al, Isolation, sequene and overexpression of the gene encoding NAD–dependent formate dehydrogenase from the methylotrophic yeast *Candida methylica*, Gene, 1995, 162, 99–104.*

Y. Sakai et al., *Journal of Bacteriology*, vol. 180, No. 22, Regulation and Physiological Role of the DAS1 Gene, Encoding Dihydroxyacetone Synthase, in the Methylotrophic Yeast *Candida boidinii*, pp. 5885–5890, (Nov. 1998).

* cited by examiner

*Primary Examiner*—Nashaat T. Nashed
*Assistant Examiner*—Malgorzata A. Walicka
(74) *Attorney, Agent, or Firm*—Foley & Lardner

(57) ABSTRACT

This invention relates to a promoter for dihydroxyacetone synthase gene from *Candida boidinii*; an expression cassette or vector comprising the promoter and a heterologous gene; a transformant transformed with this vector; and a method for producing an expression product of the heterologous gene which comprises culturing the transformant to express the heterologous gene.

12 Claims, 10 Drawing Sheets

FIG. 2

```
-1843                    GAA TTCAAAATGT GGAGAAAAGA AATCAGTTTT CTCTTATTTT -1801
-1800 AAGACAGGCA TGATGCTGTG TTATTAAAAA GATGTGTATA TTTGATTGGT TCATTAAAAT -1741
-1740 TTTAAAATAT GACTAAGCTA AATGATAATT TATGTTTATT TTTCCACTAG ATGCTAATTG -1681
-1680 TCTAGAACAA AAACTAAAAA AATCAATCTT TTCAATGTGT CCGCTATTCC GCTCCAATGA -1621
-1620 AGTGATGATT CTGTTCCGTG GAAAGCAGAA TAATTAAAAT GCCAACAAAG ATTAAGATAT -1561
-1560 GGCTATTTTA GGAATGCAGA AAGTATGATC ATGATGACAG ATTTAACCTA TTGTCTGTTA -1501
-1500 TGTAATCTTT TAAATTTTAT AATTTTTATT TATTTATTTC TTGATTCAAT TAATTTTATC -1441
-1440 TGACTCTTTT CTCTTGGAAA AATACTCATT GAGGTGAAAT TGTGGAGTCA ATTACCGGTC -1381
-1380 AACAAAATGG GAAACAGTTT ATGTGTATTT TTGGTACGTA CATATCTGCA ATCGTGCTGC -1321
-1320 TTCTGACGTT TTCAAAACAT AAGAAATTTT GAAATTTTTT TTGCAATATA ACAATGACAC -1261
-1260 AATAGCCATT GTTTGACAAA ATTTATTAAA AGCAACGTAA CTAACCTCTT TTAAAGATTT -1201
-1200 GTAACTTGTA GCCGACCTTC CAGAACTCTG ACAGTAAAAT ACGCTTGGCC GAACCTCGCC -1141
-1140 TGCGATTAGT GATCCGCCAG TAGGTGCCAG ATTTTGCGGC TTACCTAATA TTTGGTGGAC -1081
-1080 CTCTCAGTTG CATTTCAGCC GACTGTCCTA TGTGGCTGAA TATCATTTTG CCTGTCGGCT -1021
-1020 TCTTCCCAGA AATGTAGGCT CCCTATTCCA AAAGGGAAA TCGGCCGAAT CCGTTTGTTC  -961
 -960 AACATTGTT TCCTTGGATT AGCGTAGTCT TCAGTCAAGT GGACTGGATT TCAAGGGATA   -901
 -900 AACTGGGCTG AACTGGTGCG TGCAGGATAT GAAATGAAT ATGAATAATT GGTAATTCAG   -841
 -840 TCAACATGGC TAAATCGGTT CTGGATTATT GCAAATGCTT TTCAGAGAAT TAAAGTTGGT   -781
 -780 TTGGGGTAT TTTCAATGTG TGAGTTTATA TTTTCCCACT CCGTGTTGTT CCCCTTACAG    -721
 -720 TACTACAAAA TTTGCATAGC TTTCAGCATA CGGTGGATAT TTATTTCACC TATGATATAG   -661
 -660 GAAACCATAA TAATAGTAAT ACGTTAAAGT TCATTTTATT GAGACTACGC AAATTTTACC   -601
 -600 GTCTCATAAT TCAATAACTA AATCCGAATG GTCAATCGAA ATTTAAACTT AGTTTGGATA   -541
 -540 GTTTCTTATT CTTATCCCCT CTTTGCGCTA ACAGATTGTT TTTTTCTTTT GCAATTATTT   -481
 -480 TTTTATATCA TTTTTCAGTT TTAACCATTA ACCCCCCTAT TAATTAAAAG ATAATTATAC   -421
 -420 TTACCTTATT ATTTGAAAAA TTAACCCCAT ATTTAATCAA TTAGCCATTT TAATTTCTTT   -361
 -360 TTTTAATGTT ATCGTCTAAA TTCTCATCCT GTAGGTTAAT TTTATATTTC TTATTATTTT   -301
 -300 TGTTTTATCT TTTGCCGACG ACCCTTTTTT TACTTTTTTT TATAGGCAAA TAATTAAATG   -241
 -240 TAGGTTCATT TAACATTTTT CTTTTTTTTC TGAAAGTATA TAAGAAATTT AAAATCACCA   -181
 -180 ATTTTTATTT TAAATTTATT TATTCATTTT ATTTTTATTT CTATCTATCT ATCTATCTTT   -121
 -120 AAATATCATT ATTAAATTAT AAGAATAATT AATTTTTATT TGTTCATATA ATTTTATAAG    -61
  -60 AGAAAAAACA ACTTTAGAGA AAACAAAAA GATAATAAAT TATTAAAAAA AATTACAAAA     -1
```

CANDIDA BOIDINI DIHYDROXYACETONE SYNTHASE PROMOTER

TECHNICAL FIELD

The present invention relates to a promoter for dihydroxyacetone synthase gene (also referred to as DAS) from *Candida boidinii*; a gene expression cassette containing said promoter, a heterologous gene and a terminator; an expression vector containing said gene expression cassette; a transformant transformed with said vector; and a method for producing a heterologous gene product using said transformant.

BACKGROUND OF THE INVENTION

Methanol-assimilating yeasts are those capable of growing on a medium containing methanol as a sole carbon source. The methanol metabolism in the methanol-assimilating yeasts is performed as follows. In the first reaction formaldehyde and hydrogen peroxide are produced from methanol and oxygen by alcohol oxidase. The hydrogen peroxide produced is decomposed by catalase into water and oxygen. The formaldehyde, on the other hand, is oxidized eventually into carbon dioxide via actions of formaldehyde dehydrogenase, S-formylglutathione hydrolase and formate dehydrogenase, and NADH produced in these reactions is utilized as an energy source for cells. Simultaneously, the formaldehyde is condensed with xylulose-5-phosphate by dihydroxyacetone synthase to be converted into glyceraldehyde-3-phosphate and dihydroxyacetone which are then converted to cell constituents via the pentose phosphate pathway.

When the methanol-assimilating yeasts are cultured in the presence of methanol, the above-mentioned alcohol oxidase, dihydroxyacetone synthase and formate dehydrogenase are produced in significant amounts and their contents reach about 40% of the intracellular soluble proteins. Because a large scale cultivation of the methanol-assimilating yeasts can be done with inexpensive methanol as described above and because they possess methanol inducible promoters with a strong transcriptional activity not observed in other yeasts, the methanol-assimilating yeasts can be considered to be yeasts suitable for a heterologous gene expression system.

*Candida boidinii* is one of the methanol-assimilating yeasts. This yeast is used for studying a method for expressing a heterologous gene by use of a regulatory region of an alcohol oxidase gene or a formate dehydrogenase gene (see JP-A-5-344895 and International Publication WO97/10345).

Dihydroxyacetone synthase, as well as alcohol oxidase or formate dehydrogenase, is an enzyme produced in a significant amount, but no knowledge about expression control of this enzyme has been obtained so far. There is a need for a promoter of this enzyme to elucidate the expression control of this enzyme and to express a heterologous gene efficiently using its strong transcriptional activity.

The object of this invention is to provide a promoter with a strong transcriptional activity to express a heterologous gene; an expression vector containing said promoter; a host cell transformed with said expression vector; and a method for producing an expression product of heterologous gene using said host cell.

The present inventors did intensive research to elucidate the expression control system of a dihydroxyacetone synthase gene from a methanol-assimilating yeast *Candida boidinii* in order to effectively express a heterologous gene. As a result, the inventors found a promoter sequence with a strong transcriptional activity, achieved high expression of the heterologous gene using this sequence, and thereby arrived at the completion of the present invention.

SUMMARY OF THE INVENTION

The present invention relates to a promoter for dihydroxyacetone synthase gene from *Candida boidinii*, which substantially comprises a nucleotide sequence shown in SEQ ID:1. More specifically, the promoter of this invention substantially comprises a continuous 498 bp nucleotide sequence of SEQ ID NO:1, 364 to 861. Examples of this promoter include, but are not limited to, those substantially comprising a continuous 861 bp nucleotide sequence of 1 to 861, a continuous 1281 bp nucleotide sequence of 1 to 1281, and a continuous 1843 bp nucleotide sequence of 1 to 1843, all of which contain the region of the continuous 498 bp nucleotide sequence from 364 to 861 of SEQ ID NO:1. In addition, a sequence that does not contain a sequence of 364 to 861 in SEQ ID NO: 1 but possesses a promoter activity falls into the scope of this invention (FIG. 5).

As used herein, the term "substantially comprises a nucleotide sequence" means that the nucleotide sequence of SEQ ID NO:1 may have mutations, such as substitution, deletion, addition or insertion insofar as a desired promoter activity can be obtained to some degree. For example, the nucleotide sequence of SEQ ID NO:1 in which "A" at position 3 have been substituted by "T" also falls into the scope of this invention as long as the desired promoter activity can be obtained. That is, the present invention also includes a mutated or modified gene having a homology of 70% or higher, preferably 80% or higher, more preferably 90% or higher to the above defined nucleotide sequence of SEQ ID NO:1 and having a desired promoter activity.

The present invention also provides an expression cassette comprising the promoter and a heterologous gene. This expression cassette may further contain a terminator sequence or may contain a selectable marker sequence (e.g., a drug-resistant gene) or a ribosome binding site if necessary.

Further the present invention relates to an expression vector which enables the expression of a heterologous gene containing the above expression cassette.

The term "a heterologous gene" as used herein means any gene to be expressed. Such heterologous genes include, but are not limited to, an acid phosphatase gene, α-amylase gene, various interferon genes, erythropoietin gene, and granulocyte colony stimulating factor gene. These genes may be obtained by any techniques.

The present invention further relates to a transformant transformed with said expression vector.

Further, the present invention relates to a method for producing an expression product of the heterologous gene, comprising culturing said transformant in an appropriate medium, and recovering the expression product of the heterologous gene from the cultured cell. Such a medium includes, but is not limited to, media containing, as a carbon source, methanol and methanol supplemented with glycerol.

This specification contains the whole or part of the content described in the specification and/or drawings of Japanese Patent Application No. 10-37263, which is the priority claimed in this application.

BRIEF DESCRIPTION OF THE DRAWINGS

FIG. 2 shows a nucleotide sequence upstream from an ATG initiation codon for translation of the determined dihydroxyacetone synthase gene. In the sequence the number "−1" corresponds to the 3' terminus of the nucleotide sequence.

DETAILED DESCRIPTION OF THE INVENTION

Figure 1:
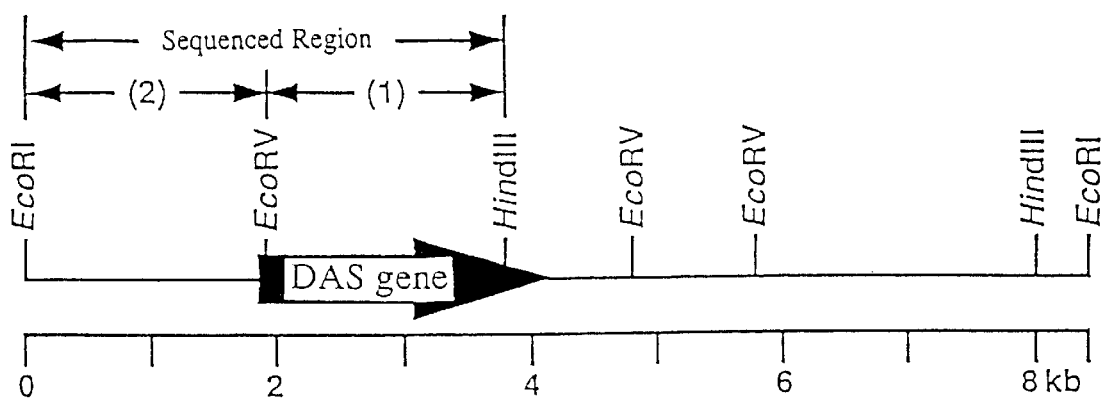
FIG. 1 shows a restriction enzyme map of the plasmid pDAS1 containing a dihydroxyacetone synthase gene (DAS).

The present inventors have elucidated a nucleotide sequence of dihydroxyacetone synthase gene from *Candida boidinii* together with its promoter, isolated the promoter, constructed an expression vector, produced a transformant using this expression vector, allowed a heterologous gene to express, and confirmed that this expression is induced by methanol likewise the induction by dihydroxyacetone synthase from *Candida boidinii*.

The present invention will be described in more detail.
(1) Cloning of Dihydroxyacetone Synthase Gene A starting material to obtain a gene of the present invention is illustratively *Candida boidinii*, particularly *Candida boidinii* S2 AOU-1 strain (Tani, Y. et al, Agri. Biol. Chem., 49, 2699, 1985).

Cloning process of this invention can be performed according to a known method (Molecular Cloning (1989), Methods in Enzymology 194 (1991)). For example, the cloning step can be carried out as follows: a DNA fragment derived from the total DNA of the above yeast or a cDNA fragment synthesized from mRNA of the above yeast is inserted into a gene transfer vector; this vector is introduced into a host cell to construct a gene library of the above yeast; a desired clone is selected from this gene library; and this clone is amplified.

(a) Preparation of Gene Library of the Yeast

The total DNA can be extracted from the yeast, for example by preparing a protoplast of the yeast, and purifying DNA from the protoplast according to a standard technique, such as DNA extraction, which includes removal of cell residues and subsequent alcohol precipitation at high salt concentration, and phenol-chloroform extraction and subsequent alcohol precipitation. Although DNA can be extracted by disrupting cells with glass beads etc. without previously preparing a protoplast, the above protoplast method is preferably carried out for easiness of preparation of high-molecular-weight DNA. A genomic library can be obtained by partially digesting the resulting chromosomal DNA with suitable restriction enzymes (e.g. Sau3AI), then ligating it to a suitable vector, and transforming the vector into a suitable *E. coli* host.

Preparation of cDNA derived from the above yeast can be carried out according to a standard cDNA preparation method using a yeast cell on growth phase in which a gene of interest is expressed. An adapter or a linker is added to each terminus of the resulting cDNA so that the cDNA can be cloned into a vector using a suitable restriction enzyme (e.g. EcoRI). After ligation of the DNA, the vector is transformed into a suitable host, thereby obtaining a cDNA library. Examples of such a vector include commercially available plasmids, such as pBR series, pUC series, and Bluscript series, which are known as a vector for constructing a gene library. Further a wide range of phage vectors such as gt and EMBL series as well as cosmids etc. can be employed. The host to be transformed or transduced with the vector constructed for preparation of the gene library can be selected depending on the type of the vector.

(b) Selection of Clone

A clone containing the desired dihydroxyacetone synthase gene can be selected and obtained from the above-described gene library by techniques such as colony hybridization, plaque hybridization, etc. using a labeled probe containing a unique sequence of the dihydroxyacetone synthase gene. In addition, a clone expressing the desired dihydroxyacetone synthase gene can be selected and obtained by techniques such as immunoscreening method using an antibody which specifically binds to dihydroxyacetone synthase.

A sequence unique to the dihydroxyacetone synthase gene used in a probe can be obtained by synthesizing a pair of oligonucleotides each corresponding to an amino acid sequence of the dihydroxyacetone synthase protein purified from *Candida boidinii*, then conducting polymerase chain reaction (PCR Technology. Henry A. Erlich, Atockton press (1989)) using the oligonucleotide pair as primers and using a chromosomal DNA of *Candida boidinii* as a template, thereby amplifying specifically a target DNA fragment. Alternatively, to obtain the DNA fragment, synthetic oligonucleotide may be used as a probe.

An antibody which specifically binds to dihydroxyacetone synthase can be obtained as follows. First dihydroxyacetone synthase purified according to a known method (Kato, N. et. al., Biochem. Biophys. Acta., 715, 143 (1982)) is injected to an animal such as a rabbit for immunization. The immunized animal is bled, and antiserum is isolated from the blood by centrifugation. The target antibody can also be obtained by purifying the antiserum as described above by purification methods, such as salting out, ion exchange chromatography, gel filtration chromatography, and affinity chromatography.

The nucleotide sequence of the target gene obtained in the manner as described above can be determined and confirmed by e.g. the chemical modification method of Maxam-Gilbert (Maxam-Gilbert, Methods in Enzymology, 65, 499 (1980)), the dideoxynucleotide chain termination method (Messing, J. and Vieire, J., Gene, 19, 269 (1982)) or their automated modified methods.

(2) Isolation of Promoter Region

To isolate the promoter region, the above-obtained target DNA can be cleaved off using restriction enzymes. Generally speaking, however, suitable restriction enzyme sites are not always located at convenient sites. As an alternative method, there is a method wherein the DNA is cleaved with DNase in the direction from a restriction enzyme site toward the promoter in the coding region so that clones with a suitably cleaved fragment are selected. Recently, a desired promoter region has been able to be easily obtained by PCR amplification with oligonucleotide primers having restriction enzyme recognizing sites previously provided at their termini.

Alternatively, these regions can be chemically synthesized based on the sequence as described in this specification. In addition, a semisynthetic promoter can also be produced by linking a chemically-synthesized partial region to cloned DNA by using a restriction enzyme site.

The promoter sequence of dihydroxyacetone synthase gene includes SEQ ID NO:1 but is not limited thereto so far as the sequence substantially bears transcriptional activity. The nucleotide sequence can be modified by deletion, insertion, substitution, addition, or the like. This modification can be made using a known mutagenesis method, such as site-directed mutagenesis which may be combined with PCR (F. M. Ausubel et al., Short Protocols in Molecular Biology, Third ed.: A Compendium of Methods from Current Protocols in Molecular Biology, John Wiley & Sons, Inc. 1995.)

(3) Construction of Expression Vector

The promoter sequence obtained as described above is inserted into an appropriate vector together with a structural gene for heterologous protein, and/or a terminator sequence, and a selectable marker gene. The resulting vector is used as a vector for expressing the heterologous gene. The vectors used herein include, but are not limited to, *E. coli* plasmid vectors such as the known vectors, i.e. pBR series, pUC series, and Bluescript series. The terminator sequence and selectable marker gene, which can function in a host, can be easily determined by those skilled in the art. The terminator sequence used herein includes e.g. an actin gene terminator and a formate dehydrogenase gene terminator. The selectable marker gene includes genes resistant to antibiotics such as G418, and genes that complement auxotrophy of a host such as URA3 and LEU2.

Elements of the expression vector can be easily inserted by those skilled in the art with reference to examples described below or by utilizing usual techniques.

(4) Preparation and Culture of Transformant

A transformant of this invention can be prepared by introducing a recombinant expression vector as described above into an appropriate host cell.

The hosts used include, but are not limited to, prokaryotes or eukayotes such as *Escherichia coli, Bacillus subtilis*, and yeasts. The preferable host is a yeast, more preferably methanol-assimilating yeast, and specifically is *Candida boidinii*. A plasmid can be introduced into such a host cell by methods generally used for transformation. Examples of such methods include the protoplast method, lithium method, electroporation method and calcium method.

The expression vector of the present invention may be integrated into a host chromosomal DNA. Further a vector having autonomously replicating sequence capable of self-replication can be used as the expression vector and allowed to exist as a plasmid in a host cell. The copy number of a heterologous gene present in a host cell may be one or two or more.

The gene expression product of interest can be obtained by culturing the so-obtained transformant in an appropriate medium and purifying from the cell culture.

The medium for the transformant of the present invention, capable of inducing expression of a heterologous gene by methanol, is as follows. That is, the medium contains, in addition to methanol, one or more nitrogen sources, such as yeast extracts, trypton, meat extracts, peptone, casanino acid, and ammonium salt; inorganic salts, such as phosphate, sodium, potassium, magnesium, calcium, iron, copper, manganese, and cobalt. Further if necessary the medium may be supplemented with trace amounts of nutrients, such as vitamins, amino acids, nucleotides; and glucid raw materials such as glycerol.

The preferred pH range of the medium is 5 to 8. The culture temperature normally ranges from 15 to 45° C., preferably around 28° C. The culture time is about 24 to 1,000 hours. The culture can be performed by a method selected from static culture, shaking culture, stirring culture, or batch culture or continuous culture under aeration.

After the culture is completed, the gene product can be recovered from the culture by standard protein purification techniques. For example, the gene product, when produced intracelluraly, is recovered by disrupting the cell by standard techniques, such as ultrasonication, grinding, or disrupting under pressure, to obtain a crude protein solution which contains the gene product. If necessary a protease inhibitor is added. The gene product produced in the culture supernatant can be recovered from the culture fluid. That is, the obtained solution can be filtered or centrifuged to remove solids, thereby obtaining a crude protein solution. If necessary nucleic acids are removed from the solution by treating with protamine. Then the target protein can be isolated and purified from the crude protein solution by suitably combining purification techniques, such as salting out, solvent precipitation, dialysis, ultrafiltration, gel electrophoresis, ion exchange chromatography, gel filtration chromatography, reverse phase chromatography, and affinity chromatography.

The present invention provides a promoter having strong transcriptional activity that leads to expression of a heterologous gene. Culture of a transformant obtained by use of the expression vector which comprises said promoter and a heterologous gene of interest results in efficient expression and production of various useful proteins.

The present invention will be illustrated in more detail by the following examples to which, however, the invention is not limited.

EXAMPLES

Example 1

Cloning of Dihydroxyacetone Synthase Gene from *Candida boidinii*

In this example, a dihydroxyacetone synthase gene was obtained from *Candida boidinii* S2 AOU-1 (Tani, Y. et. al., Agri. Biol. Chem., 49, 2699 (1985)) and its nucleotide sequence was determined.

(1—) Construction of Probe

A cDNA was obtained from *Candida boidinii* ATCC 32195 strain which had been cultured in a medium containing methanol as a carbon source until its mid-logarithmic growth phase. The cDNA was integrated into λgt11

(Stratagene) so as to construct a cDNA library. Isolation of mRNA and synthesis of cDNA were performed according to a known method (Lisa, J., Garrard and Joel, M., Goodman, J. Biol. Chem., 264, 13929 (1989)). A recombinant phage DNA was packaged. Then E. coli Y1090r-strain (Stratagene) was infected with this phage DNA, thereby leading to plaque formation.

The dihydroxyacetone synthase purified according to the method described by Kato, N. et. al. (Biochem. Biophys. Acta., 715, 143 (1982)) was injected to a rabbit for immunization, thereby obtaining serum containing anti-dihydroxyacetone synthase antibodies.

Immunoscreening was performed on the plaques formed by the recombinant phage using the above anti-dihydroxyacetone synthase antibody according to a standard technique (Sambrook, J. et. al., Molecular cloning, $2^{nd}$ ed., Cold Spring Harbor Laboratory U.S.A. (1989); or Glover D. M., DNA cloning, IRL Press, Oxford (1985)). Goat anti-rabbit IgG antibody labeled with horseradish peroxidase (Bio-Rad) was used as a secondary antibody. A positive clone was obtained from the plaque developing color by peroxidase reaction.

The recombinant phage DNA was obtained from the positive clone according to a standard technique (Sambrook. J. et al., Molecular cloning $2^{nd}$ ed., Cold Spring Harbor Laboratory U.S.A. (1989)). The obtained DNA was cleaved with EcoRI, and subjected to agarose gel electrophoresis. Thus 2.2 kb dihydroxyacetone synthase cDNA fragment was recovered from the gel.

(1-2) Construction and Screening of Library

Chromosomal DNA from *Candida boidinii* S2 AOU-1 strain prepared according to the method of Cryer, D. et. al., (Methods Cell Biol., 12, 39 (1975)) was cleaved with various restriction enzymes and subjected to Southern hybridization using the DNA fragment obtained as a probe in (1-1) above. The probe was labeled with a radioisotope using a mega-primer DNA labeling system (Amersham), and the hybridization was carried out by standard techniques (Sambrook, J., et al., Molecular cloning 2nd ed., Cold Spring Harbor Laboratory U.S.A., 1989). As a result, approximately 8.3 kb EcoRI fragment was presumed to contain a dihydroxyacetone syntahse gene. To clone the fragment, a library was constructed.

The chromosomal DNA of *Candida boidinii* was cleaved with EcoRI and subjected to agarose gel electrophoresis, thereby recovering an approximately 8.3 kb DNA fragment from the gel. The recovered DNA fragment was inserted into the EcoRI cleavage site of pBluescript II SK+. The resulting recombinant plasmid was transformed into E. coli JM 109 strain according to the method of Hanahan (Gene, 10, 63 (1980)) to construct a library.

The library was screened by colony hybridization. Positive clones containing plasmid pDAS1 were selected by autoradiography.

(1-3) Nucleotide Sequencing

A restriction enzyme map of plasmid pDAS1 was prepared (FIG. 1). Analysis by Southern hybridization was conducted using dihydroxyacetone synthase cDNA fragment as a probe, which was derived from *Candida boidinii* ATCC 32195 strain described in (1-1) above. Then a nucleotide sequence in an approximately 1.8 kb region between EcoRV-HindIII indicated as (1) in FIG. 1, presumed to contain dihydroxyacetone synthase gene, was determined using a dye primer cycle sequence kit and a dye terminator cycle sequence kit (Perkin-Elmer). Deletion mutants for nucleotide sequencing were obtained using a deletion kit for kilosequence (Takara Shuzo Co., Ltd.). As a result, the amino acid sequence deduced from the resulting nucleotide sequence contained a region with high homology to the amino acid sequence of dihydroxyacetone synthase (Janowicz, Z., A., Nucleic Acids Res., 13, 3043 (1985); or the gene accession number P06834) from the methanol assimilating yeast *Hansenula polymorpha*, which has already been reported; and the same amino acid sequence contained a sequence identical to the N-terminal amino acid sequence (MALAKAASINDDIHDLTMRAF; SEQ ID NO: 23) as determined by the purified dihydroxyacetone synthase. Therefore, it was assumed that the target dihydroxyacetone synthase gene was present at the position indicated with an arrow in FIG. 1. Further, to determine a nucleotide sequence of the 5' upstream region of dihydroxyacetone synthase gene, a nucleotide sequence of the EcoRI-EcoRV region shown with (2) in FIG. 1 was determined in the same manner. This region contained a 1,843 bp nucleotide sequence that was located upstream from a 39 bp nucleotide sequence (ATGGCTCTCGCAAAAGCTGCTTCA ATTAACGATGATATC; SEQ ID NO:3) corresponding to the N-terminal 13 amino acids (MALAKAASINDDI; SEQ ID NO:2) of dihydroxyacetone synthase. The 1,843 bp nucleotide sequence in the 5' upstream region of ATG-initiation codon as determined in this example is shown in FIG. 2. In FIG. 2, nucleotide numbers of the sequence are numbered so that "A" at the 3' terminus represents "−1".

Example 2

Expression of Heterologous Gene Using Dihydroxyacetone Synthase Gene Promoter

This example describes transformation of an expression vector into a *Candida boidinii* strain. The vector for expression of acid phosphatase gene (PHO5) derived from *Saccharomyces cerevisiae* was produced using a promoter region for dihydroxyacetone synthase gene (DAS) from *Candida boidinii* S2 AOU-1 strain.

(2-1) Preparation of Plasmid for Expression of Acid Phosphatase

A promoter region of dihydroxyacetone synthase gene was isolated using PCR. The following two oligonucleotides were synthesized as PCR primers based on information in FIG. 2 (or SEQ ID NO:1):

PDAS5:GGGCTCGAGGAATTCAAAATGTGGAGA AAAGAAAATC (SEQ ID NO:4);

PDAS3:CCCGCGGCCGCTTTTGTAATTTTTTTTAAT AATTTATTATCTTTTTGTTTTTC (SEQ ID NO:5).

Figure 3:
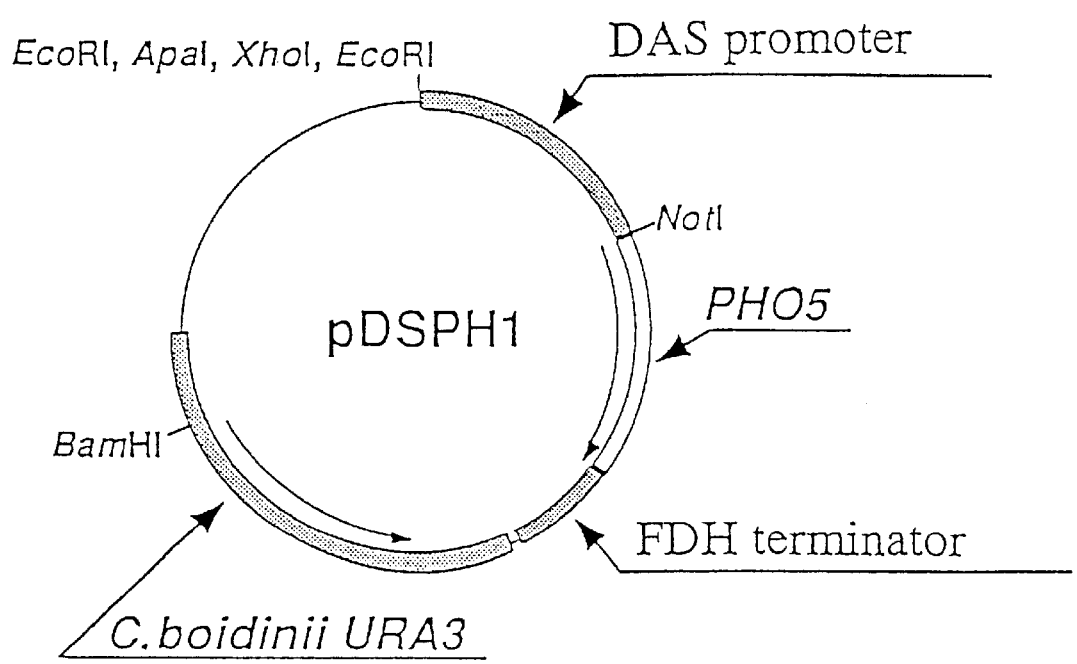
FIG. 3 shows the structure of the plasmid pDSPH1.

Plasmid pDAS1, primer PDAS5, and PDAS3 were mixed, and subjected to PCR ((30 seconds at 94° C., 1 minute at 55° C., and 2 minutes at 72° C.)×20 cycles) using Ex Taq polymerase (Takara Shuzo Co., Ltd.). The amplified DNA fragment was cloned into pT7 Blue T-Vector (Novagene) and isolated as a XhoI-NotI fragment. This fragment was inserted between XhoI and NotI of plasmid pPUF 1 (as described in the International Publication WO97/10345), which contains URA3 gene as a marker gene and is a plasmid for expressing an acid phosphatase by FDH promoter/terminator. The obtained plasmid was named DSPH1 (FIG. 3). The above-mentioned plasmid pPUF 1 can be easily produced according to methods described in the International Publication WO97/10345. The FDH terminator, URA3 gene, and PHO5 gene can be chemically synthesized based on the sequence disclosed in the International Publication WO97/10345, Sakai Y. et. al., J. Ferment. Bioeng., 73, 255–260 (1992), or Arima, K. et. al., Nucleic Acids Res., 11, 1657 (1983).

(2—) Transformation

A strain with mutated URA3 gene, *Candida boidinii* KST2515 strain (WO97/10345), was used as a host strain. Other *Candida boidinii* strains, such as IFO 10035 strain, can also be used for transformation with said plasmid because a strain with mutated URA3 gene can easily be obtained from such strains according to a known method (Sakai Y. et. al., J. Bacteriol., 173, 7458 (1991)).

Figure 4:
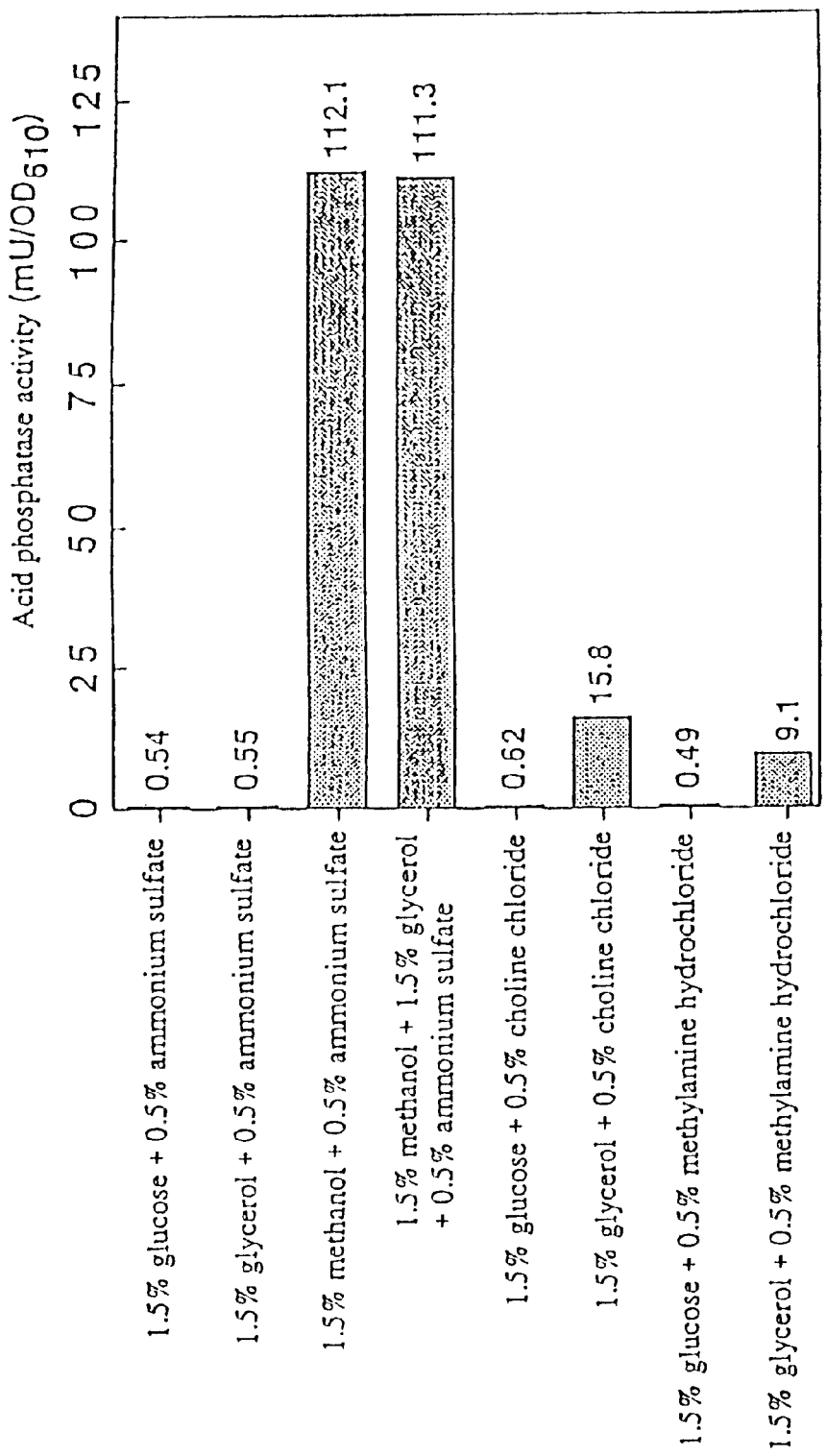
FIG. 4 shows activities of acid phosphatase expressed under the control of DAS promoter which is derived from a transformant cultured with various carbon and nitrogen sources.

Five µg of plasmid pDSPH1 obtained in (2-1) above was cleaved with BamHI and transformed into *Candida boidinii* KST2515 strain. Among the obtained transformants, strains containing one copy of the introduced plasmid were cultured in a medium at pH 5.5 which contains 0.17% Yeast Nitrogen Base w/o amino acids and ammonium sulfate (Difco) and various carbon and nitrogen sources shown in FIG. 4 and then the acid phosphatase activity was assayed. That is, a transformant containing one copy of the introduced plasmid was confirmed by measuring an activity of orotidylate decarboxylase that is a marker of the transformant, i.e. URA3 gene product, according to a known method (Sakai Y. et. al., J. Bacteriol., 175, 3556 (1993)), The acid phosphatase activity was measured using cell suspension itself as an enzyme, according to the method of Tohe, A. et al. (J. Bacteriol., 113, 727 (1973)). One unit of enzyme activity is an amount of enzyme to produce 1 mmole of p-nitrophenol for 1 minute at 30° C. As shown in FIG. 4, the expression of acid phosphatase was induced strongly when a carbon source was methanol. But no induction was observed with glucose or glycerol. When choline or methyl amine was used as a nitrogen source, induction was observed with glycerol as a carbon source, but no induction with glucose. It was therefore found that the dihydroxyacetone synthase gene promoter was under control different from the alcohol oxidase gene promoter or the formate dehydrogenase gene promoter because no dihydroxyacetone synthase gene promoter was induced by glycerol alone or because its induction was completely inhibited by glucose, respectively.

Example 3

Analysis of 5'-Region for Dihydroxyacetone Synthase Gene Promoter Activity

This example describes identification of a region necessary for DAS promoter to function. The *Candida boidinii* DAS promoter from which upstream region was deleted was produced. The acid phosphatase activity under control of the upstream-deletion type DAS promoter was measured.

(3-1) Construction of PHO5 Expression Plasmid Under Control of Upstream-deletion Type DAS Promoter DAS promoter from which upstream region was deleted was constructed using a deletion kit for kilosequence (Takara Shuzo Co., Ltd.) and by PCR. Plasmid pDSPH1 was cleaved with ApaI-XhoI, and treated with the deletion kit for kilosequence, obtaining PHO5 expression plasmids under control of the upstream-deletion type DAS promoter, pDSPHΔ1, pDSPHΔ2, pDSPHΔ3, pDSPHΔ4, pDSPHΔ5, pDSPHΔ6, pDSPHΔ7, and pDSPHΔ8. Then nucleotide sequences on the 5' side in DAS promoter regions of these plasmids were determined, whereby plasmids pDSPHΔ1, pDSPHΔ2, pDSPHΔ3, pDSPHΔ4, pDSPHΔ5, pDSPHΔ6, pDSPHΔ7, and pDSPHΔ8 were confirmed to contain promoter regions, which are 1,480 bp (a sequence from –1 to –1,480 as shown in FIG. 2), 878 bp (a sequence from –1 to –878 as shown in FIG. 2), 813 bp (a sequence from –1 to –813 as shown in FIG. 2), 746 bp (a sequence from –1 to –746 as shown in FIG. 2), 607 bp (a sequence from –1 to –670 as shown in FIG. 2), 524 bp (a sequence from –1 to –524 as shown in FIG. 2), 439 bp (a sequence from –1 to 439 as shown in FIG. 2), and 286 bp (a sequence from –1 to –286 as shown in FIG. 2), respectively.

To construct by PCR the DAS promoter from which upstream region was deleted, the following oligonucleotides were synthesized:

PDS1199;CCTCTTTTAAAGAATTCTAACTTGTAG CCGACC (SEQ ID NO:6);

PDS 1006;GCTTCTTCCCAGAATTCTAGGCTCCCT ATTCCAAAAAGG (SEQ ID NO:7);

PDS583;GGGGAATTCTAAATCCGAATGGTCAATCG (SEQ ID NO:8);

PDS565;GGGGAATTCGAAATTTAAACTTAGTTT GGATAG (SEQ ID NO:9);

PDS543;GGGGAATTCATAGTTTCTTATTCTTATCCC CTC (SEQ ID NO:10).

PCR ((30 seconds at 94° C., 1 minute at 55° C., 1 minute at 72° C.)×20 cycles) was performed using PDAS3 with either one of PDS1199, PDS1006, PDS583, PDS565, and PDS543 as primers, and using pDAS1 as a template. Each amplified DNA fragment was cloned into pT7 Blue T-vector (Novagene), isolated as an EcoRI-NotI fragment, and inserted between EcoRI and NotI of pDSPH1, thereby constructing plasmids pDSPHΔ1199, pDSPHΔ1006, pDSPHΔ583, pDSPHΔ565, and pDSPHΔ543. These plasmids pDSPHΔ1199, pDSPHΔ1006, pDSPHΔ583, and pDSPHΔ543 contained promoter regions, which are 1,199 bp (a sequence from –1 to –1,199 as shown in FIG. 2), 1,006 bp (a sequence from –1 to –1,006 as shown in FIG. 2), 583 bp (a sequence from –1 to –583 as shown in FIG. 2), 565 bp (–1 to –565 as shown in FIG. 2), and 543 bp (a sequence from –1 to –543 as shown in FIG. 2), respectively.

(3-2) Transformation

Figure 5:
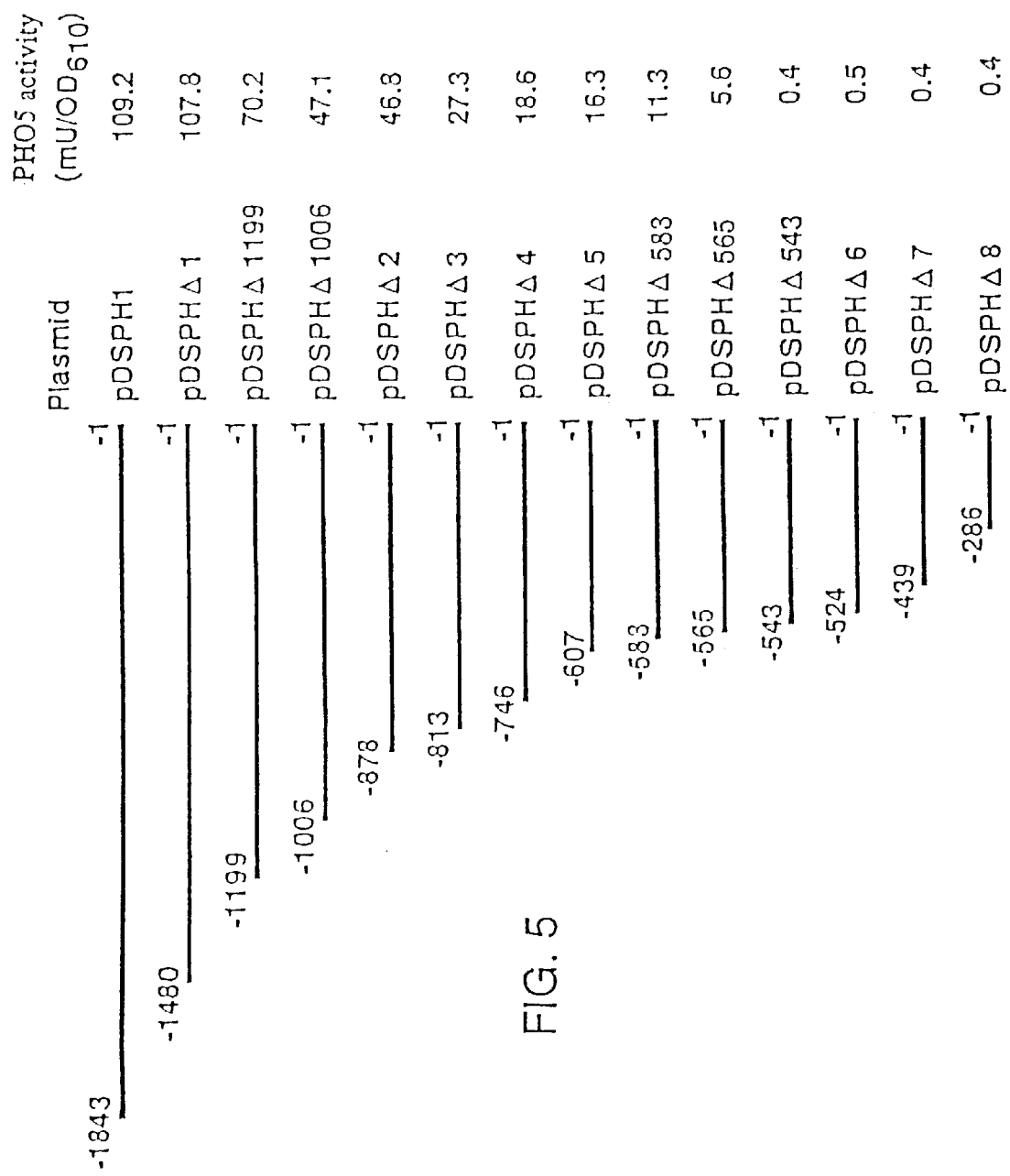
FIG. 5 shows activities of acid phosphatase expressed under the control of upstream-deletion type DAS promoters.

Five µg each of the plasmid DNA obtained in (3-1) above was cleaved with BamHI, and transformed into *Candida boidinii* KST2515 strain. The obtained transformants were screened to find those containing one copy of the introduced plasmid. The screened transformants each were cultured in a medium, pH 5.5, containing 0.67% Yeast Nitrogen Base and 1.5% methanol, and then the acid phosphatase activity was assayed. The specific activity of acid phosphatase (unit/OD610) produced by the transformants due to the respective plasmids was shown in FIG. 5. As shown in FIG. 5, the 1,480 bp region, a sequence from –1 to –1,480 as shown in FIG. 2, was required for the upstream-deletion type DAS promoter to exhibit induction by methanol at the same degree with that of wild-type promoter. It was also shown that induction activity gradually decreased as deletion proceeded. With the 543 bp promoter region, a sequence from –1 to –543 as shown in FIG. 2, the upstream-deletion type promoter hardly exhibited induction by methanol.

Example 4

Analysis of Region for Dihydroxyacetone Synthase Gene Promoter Activity Using Internal Region-Deletion Type Mutants This example describes the identification of a region necessary for DAS promoter to function. A *Candida boidinii* DAS promoter from which internal region was deleted was produced. The acid phosphatase activity under control of the internal deletion type DAS promoter was measured.

Figure 6:
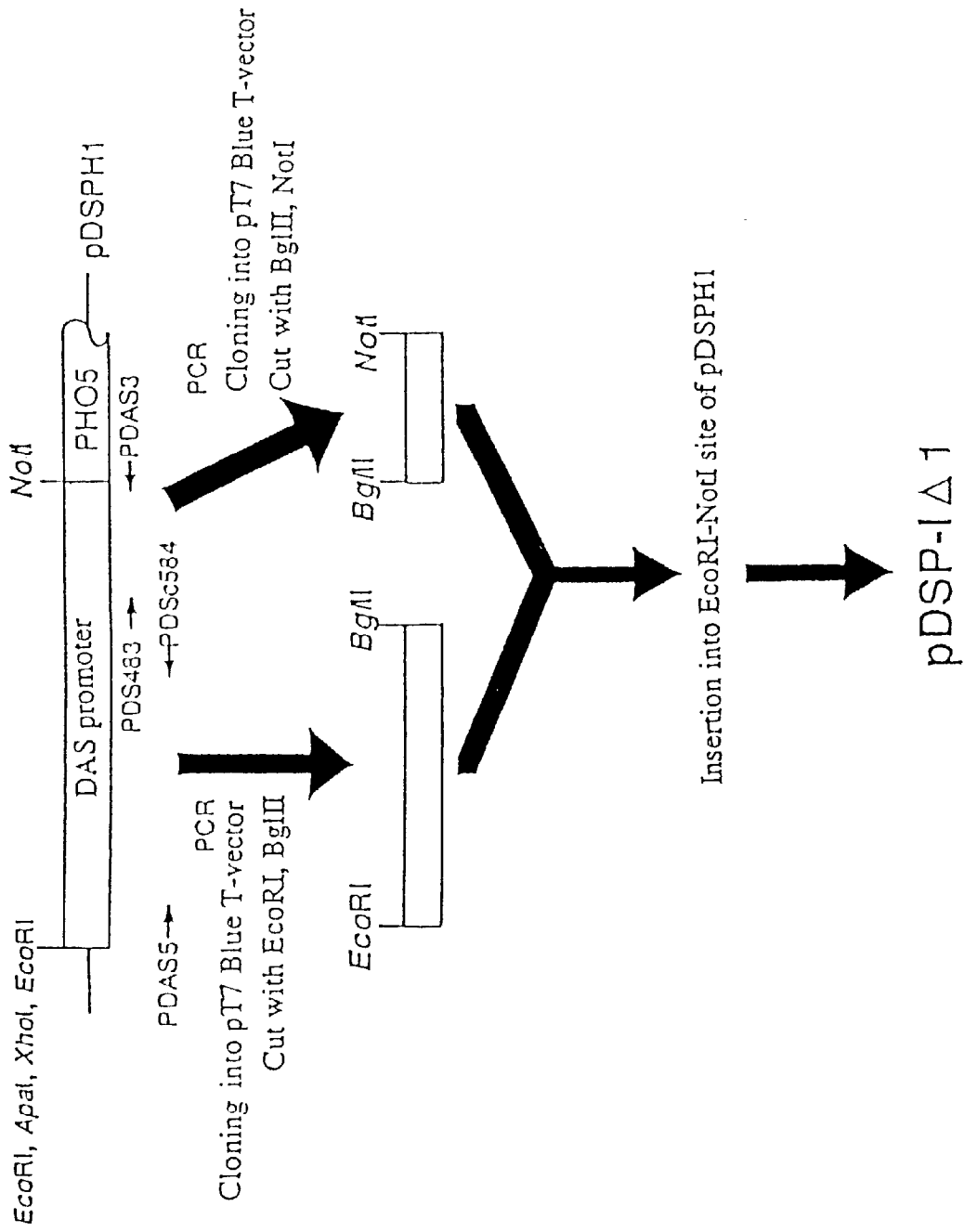
FIG. 6 shows a method for constructing the acid phosphatase-expressing plasmid pDSP-IΔ1 by DAS promoter wherein the internal region has been deleted.

(4-1) Construction of PHO5 Expression Plasmid Under Control of Internal Region Deletion Type DAS Promoter The DAS promoter from which the internal region was deleted was produced by PCR. FIG. 6 shows a method for constructing pDSP-IΔ1. To construct by PCR the DAS promoter from which the internal region was deleted, the following oligonucleotides were synthesized:

PDS483;GGGAGATCTTTTTTTATATCATTTTTCA GTTTTAACCATTAAC (SEQ ID NO:11);

PDSc584;GGGAGATCTTATTGAATTATGAGACGGT
AAAATTTGC (SEQ ID NO:12);

PDSc684;GGGAGATCTTCCACCGTATGCTGAAA
GCTATGCAAATTTTG (SEQ ID NO:13);

PDSc784;GGGAGATCTAACTTTAATTCTCTGAAAA
GCATTTGCAATAATC (SEQ ID NO:14);

PDSc884;GGGAGATCTACCAGTTCAGCCCAGTTTA
TCCCTTGAAATC (SEQ ID NO:15);

PDSc983;GGGAGATCTCCCTTTTTGGAATAGGG
AGCCTACATTTC (SEQ ID NO;16);

PDSc1184;GGGAGATCTCACCAAATATTAGGTAAG
CCGCAAAATCTG (SEQ ID NO;17);

PDSc1184;GGGAGATCTGGTCGGCTACAAGTTAC
AAATCTTTAAAAGAG (SEQ ID NO;18);

PDSc1284;GGGAGATCTAAATTTCAAAATTTCTT
ATGTTTTGAAAACGTCAG (SEQ ID NO:19);

PDSc1384;GGGAGATCTCGCTAATTGACTCCAC
AATTTCACCTCAATG (SEQ ID NO:20).

PCR ((30 seconds at 94° C., 1 minute at 55° C., 1 minute at 72° C.)×20 cycles) was performed using PDS483 and PDAS3, and using pDSPH1 as a template, thereby amplifying a region from −1 to −483 shown in FIG. 2. Each amplified DNA fragment was cloned into pT7 Blue T-vector and isolated as a BglII-NotI fragment. Further PCR ((30 seconds at 94° C., 1 minute at 55° C., 1 minute at 72° C.)×20 cycles) was performed using PDAS5 and any one of PDSc584, PDSc684, PDSc784, PDSc884, PDSc983, PDSc1084, PDSc1184, PDSc1284, and PDSc1384 as primers, and using pDSPH1 as a template. Regions amplified were from −584 to −1843, −684 to −1843, −784 to −1843, −884 to −1843, −983 to −1843, −1084 to −1843, −1184 to −1843, −1284 to −1843, and −1384 to −1843, respectively. Each amplified DNA fragment was cloned in pT7 Blue T-Vector, isolated as an EcoRI-BglII fragment, inserted together with the aforementioned BglII-NotI DNA fragment into between EcoRI and NotI of pDSPH1, thereby constructing plasmids pDSP-IΔ1, pDSP-IΔ2, pDSP-IΔ3, pDSP-IΔ4, pDSP-IΔ5, pDSP-IΔ6, pDSP-IΔ7, pDSP-IΔ8, and pDSP-IΔ9. As shown in FIG. 2, plasmid pDSP-IΔ1 contained a deletion of a region from −484 to −583, pDSP-IΔ2 from −484 to −683, pDSP-IΔ3 from −484 to −783, pDSP-IΔ4 from −484 to −883, pDSP-IΔ5 from −484 to −982, pDSP-IΔ6 from −484 to −1083, pDSP-IΔ7 from −484 to −1183, pDSP-IΔ8 from −484 to −1283, and pDSP-IΔ9 from −484 to −1383, respectively.

(4-2) Transfomation

Figure 7:
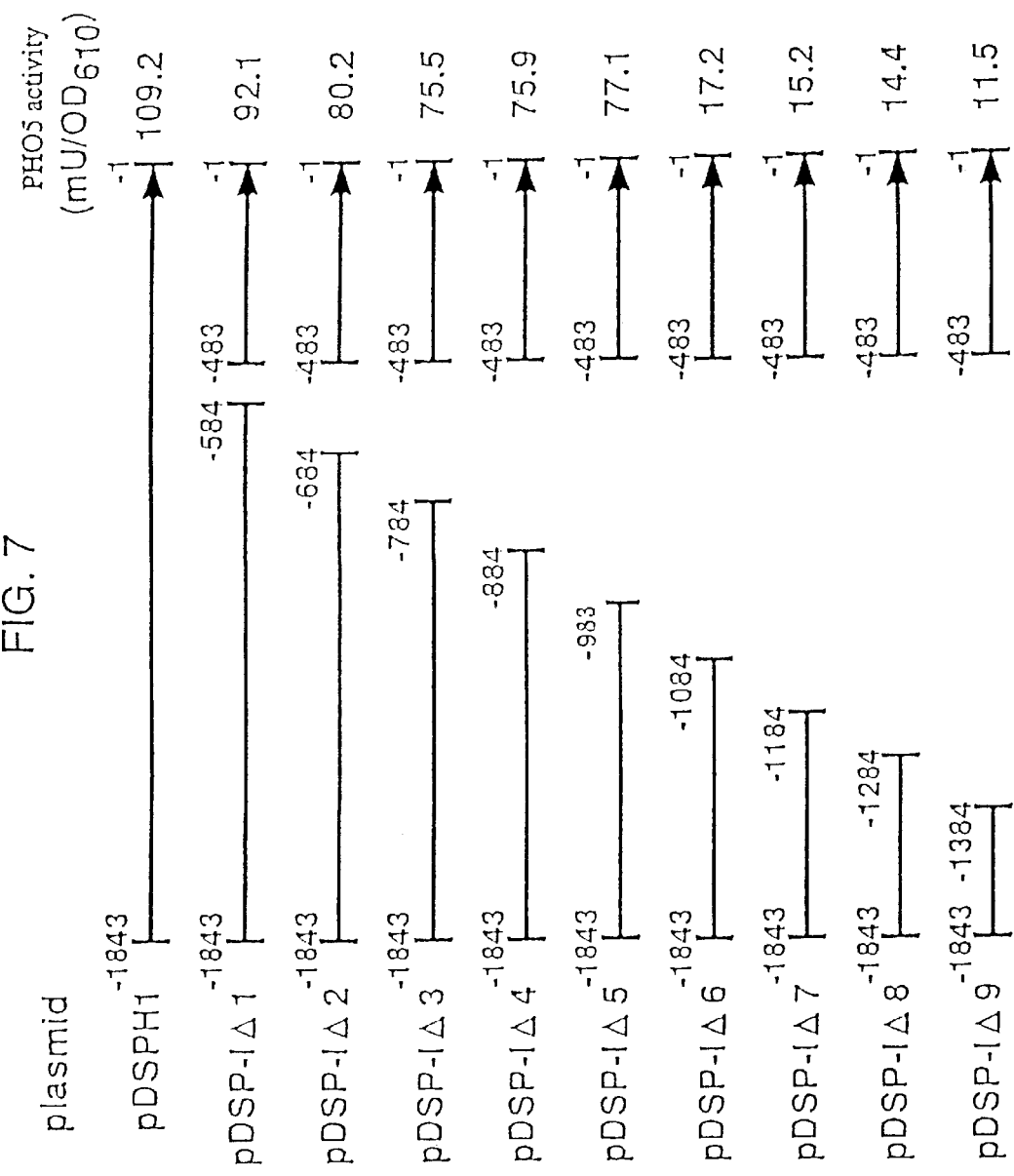
FIG. 7 shows activities of acid phosphatase expressed under the control of the DAS promoters wherein the internal region has been deleted.

Five μg each of the plasmid DNA obtained in (4-1) above was cleaved with BamHI, and transformed into *Candida boidinii* KST2515 strain. Transformants were screened to find those containing one copy of the plasmid inserted. The screened transformants each were cultured in a medium, pH 5.5, containing 1.5% methanol and 0.67% Yeast Nitrogen Base, and then the acid phosphatase activity was assayed. The specific activity of acid phosphatase (unit/OD610) produced by the transformants due to the respective plasmids is shown in FIG. 7, which indicates that the promoter activity gradually decreased as the deletion region inside the promoter increased. As deletion of the region was increased, that is, from plasmid pDSP-IΔ5 containing a deletion of the region from −484 to −982 of DAS promoter shown in FIG. 2 to plasmid pDSP-IΔ6 containing the deletion from −484 to −1083, the promoter activity significantly decreased. These results show that induction of dihydroxyacetone synthase gene promoter by methanol needs to have a region upstream from −983 in FIG. 2. As previously suggested by analysis using the 5'-deletion promoter in Example 3, it was suggested that induction of dihydroxyacentone synthase gene promoter by methanol requires possession of the promoter region from −983 to −1480, which corresponds to a sequence from 364 to 861 in SEQ ID NO:1.

Example 5

Analysis of Region for Activity of DAS Promoter Fused with Another Promoter Region This example describes identification of a region necessary for DAS promoter to function in order to confirm the results obtained in (4-2) of Example 4. For this purpose, a fusion promoter was constructed by fusing a region upstream from 861 of DAS promoter in SEQ ID NO:1 with a promoter that is not induced by methanol. Then the acid phosphatase activity under control of the fusion promoter was measured.

(5-1) Construction of PHO5 Expression Plasmid Under Control of Fusion Promoter

As shown in the results described in International Publication WO97/10345, *Candida boidinii* formate dehydrogenase gene (FDH) promoter is strongly induced by methanol. However, a 521 bp region upstream 5' of ATG initiation codon for starting translation of formate dehydrogenase gene retains very weak transcriptional activity, and in this region the induction effect of methanol was significantly lower than that in wild-type. To examine this, a fusion promoter of this region with a region assumed necessary for DAS promoter activity was constructed.

To obtain a 521 bp FDH promoter region upstream 5' of ATG initiation codon for starting translation, the following oligonucleotides were synthesized:

PF521;CCAGATCTTGATAATAAGGTATACTACAT
TTTATC (SEQ ID NO:21);

PRV3;CAATGAGCCGTTGAATTGACGAGTG (SEQ ID NO:22).

PCR ((30 seconds at 94° C., 1 minute at 55° C., 1 minute at 72° C.)×20 cycles) was performed using PF521 and PRV3, and using pPUF1 described in International Publication WO97/10345 as a template. Each amplified DNA fragment was cloned in pT7 Blue T-vector and isolated as a BglII-NotI fragment. This BglII-NotI fragment was inserted between BglII and NotI of pDSP-IΔ5 described in Example 4 (4-1) to construct an acid phosphatase expression plasmid pDSFP1 with the fusion promoter. Next pDSFP1 was cleaved with EcoRI-BglII, blunt-ended using T4 DNA polymerase, thereby constructing plasmid pPUF521 following self-ligation. The pPUF521 was a PHO5 expression plasmid with 521 bp FDH promoter region.

(5-2) Transformation

Figure 8:
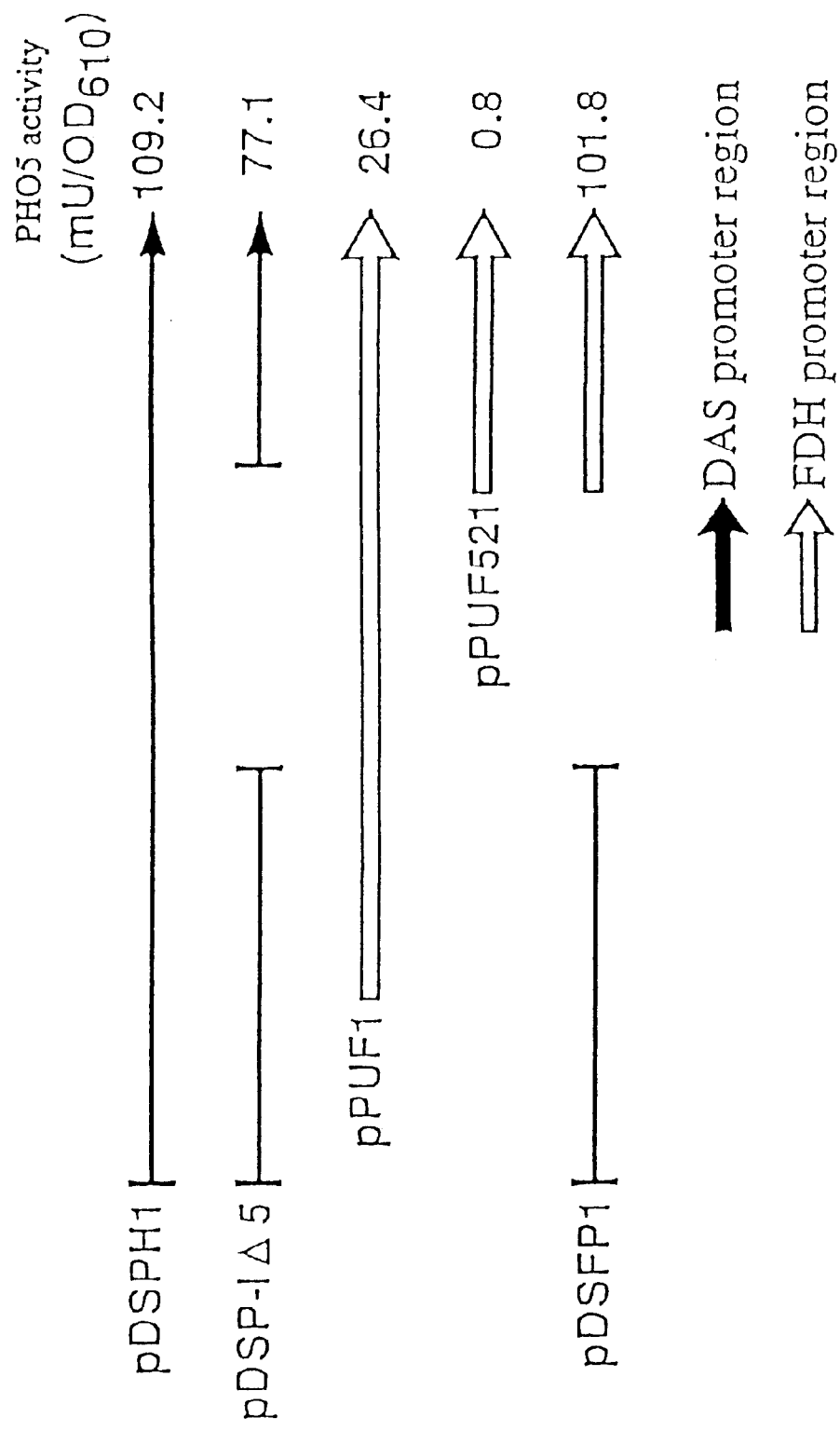
FIG. 8 shows a structure of the formate dehydrogenase gene (FDH) promoter to which a region suspected necessary for DAS promoter activity has been added; and activities of acid phosphatase expressed under the control of the promoters.

The plasmid DNAs obtained in (5-1) above, i.e. pDSFP1 and pPUF521, and pPUF1, 5 μg each, were cleaved with BamHI, and then transformed into *Candida boidinii* KST2515 strain. The obtained transformants were screened to find those containing one copy of the plasmid inserted. The screened transformants were cultured in a medium, pH 5.5, containing 1.5% methanol and 0.67% Yeast Nitrogen Base, and then the acid phosphatase activity was assayed. The specific activity of acid phosphatase (unit/OD610) produced by the transformants due to the respective plasmids is shown in FIG. 8. Ligation of a region from −983 to −1843 of DAS promoter in FIG. 2 to a 521 bp FDH promoter resulted in strong induction by methanol of the acid phosphatase activity at a comparable degree to that of wild-type DAS promoter. Therefore, it was shown that a region upstream from 861 of DAS promoter in SEQ ID NO:1 is required to exhibit an induction effect of expression by methanol.

Example 6

Change with Time in Expression of Heterologous Gene with Dihydroxyacetone Synthase Gene Promoter How expression with DAS promoter changed after induction by methanol was examined using acid phosphatase gene as a reporter gene. Further expression with alcohol oxidase gene (AOD) promoter, which is strongly induced by methanol likewise DAS promoter, was also examined and compared with the expression with DAS promoter.

The plasmid used for expressing an acid phosphatase gene derived from *Saccharomyces cerevisiae* by DAS promoter was pDSPH1 described in Example 2, and host *Candida boidinii* strain was *Candida boidinii* TK62 strain, a strain with mutated URA3 gene (Sakai Y. et al., J. Bacteriol., 173, 7458 (1991)). An acid phosphatase gene expression plasmid with AOD promoter was constructed as follows.

Plasmid pDSPH1 was cleaved with SmaI and HindIII, blunt-ended with T4 DNA polymerase, then ligated to NotI linker (Takara Shuzo. Co., Ltd.). An acid phosphatase gene was isolated as an NotI fragment, and introduced into an NotI site of an expression plasmid pNoteI (Sakai Y. et al., Biochem. Biophys. Acta, 1308, 81 (1996)) with AOD promoter. The resulting plasmid was named pAXPH1.

Figure 9:
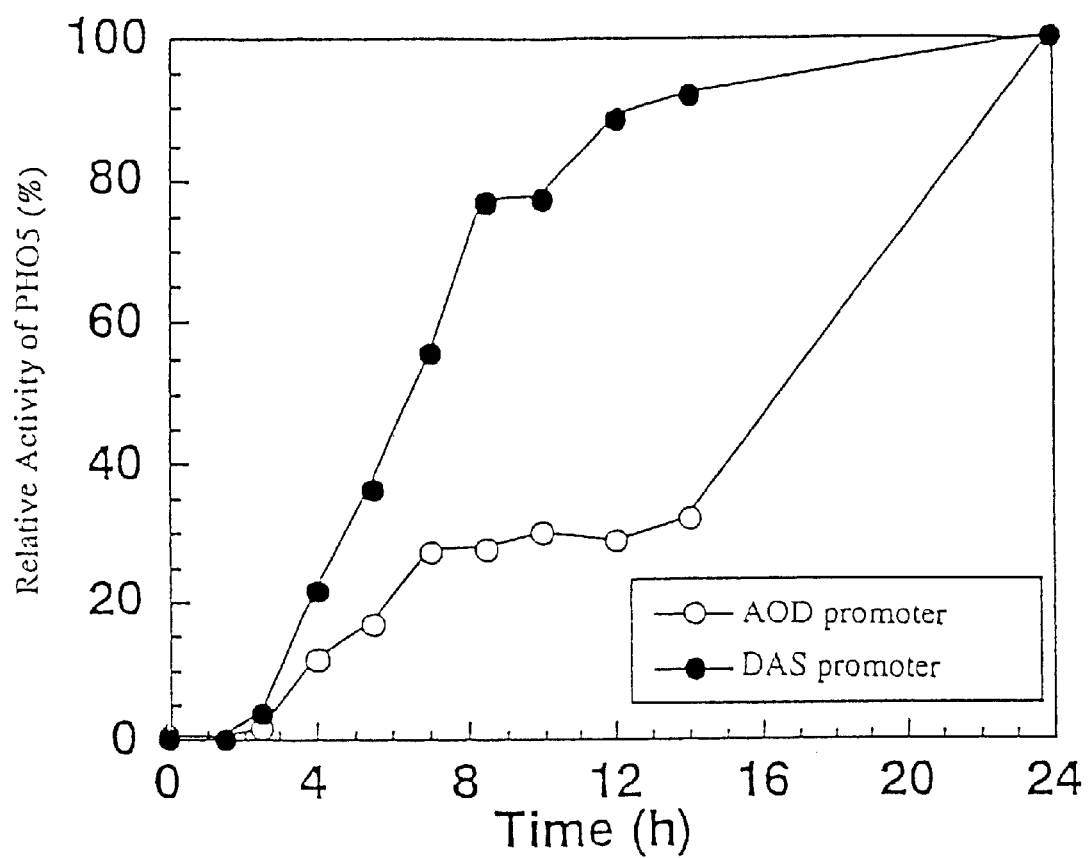
FIG. 9 shows changes with time in acid phosphatase activity after methanol induction in strains transformed with pDSPH1 (a plasmid for expressing acid phosphatase gene (PHO5) by DAS promoter) and pAXPH1 (a plasmid for expressing acid phosphatase gene by alcohol oxidase gene (AOD) promoter). The activity of acid phosphatase is defined as a relative value to the activity (as 100%) after 24 hours of induction with methanol.

Plasmids pDSPH1 and pAXPH1, 5 $\mu$g each, were cleaved with BamHI, and transformed into *Candida boidinii* TK62 strain. The obtained transformants were screened for a strain wherein one copy of the plasmid was integrated into the chromosome, by assaying for orotidylate decarbonase activity encoded by URA3 gene (Sakai Y et al., J. Bacteriol., 175, 3556 (1993)). The screened yeasts each were cultured in YPD medium for 36 hours, inoculated in a preculture medium (2% glucose, 0.67% Yeast Nitrogen Base, 0.5% Yeast Extract) to OD610 of 0.5, and then cultured for 8 hours. The preculture fluid was added to a 300 ml of an induction medium (0.5% methanol, 0.67% Yeast Nitrogen Base, 0.5% Yeast Extract) in a 3 L Erlenmeyer flask, the preculture being adjusted to OD610 of 1, and cultured at 28° C. with rotating at 320 rpm. Sampling was conducted at certain intervals, and the acid phosphatase activity produced by the cells per one OD610 was measured. Both AOD and DAS promoters showed the maximum activity 24 hours after the induction. After 24 hours, the acid phosphatase activity of the cells per one OD610 was 794 mU for DAS promoter and 459 mU for AOD promoter. Thus DAS promoter was superior to AOD promoter for acid phosphatase activity. Changes with time in relative activity of acid phosphatase is shown in FIG. 9 where a value observed after 24 hours was defined as 100. The velocity to reach the maximum activity was greater in DAS promoter than in AOD promoter.

To examine the difference in the velocity of induction, expression of acid phosphatase was tried using an alcohol oxidase gene-disrupted strain in which no methanol is metabolized. An alcohol oxidase gene region was isolated as an approximately 3.3 kb XbaI-HindIII from pMOX620 (JP-A-5-344895), and then introduced into pBluescript II SK+. This plasmid was cleaved with StyI, blunt-ended, and ligated to a fragment which was cleaved out from pSPR (Sakai Y. et al., J. Bacteriol., 174, 5988 (1992)), with SacI-XhoI and blunt-ended. The resulting plasmid was cleaved with SacI-XhoI, and transformed into *Candida boidinii* TK62 strain. The obtained transformants were subjected to Southern analysis of the chromosomal DNA for screening an alcohol oxidase gene-disrupted strain. That is, the chromosomal DNAs of the host TK62 strain and the transformed strain were cleaved with EcoRI and HindIII, and subjected to Southern analysis using a 3.3 kb DNA fragment as a probe that was obtained by cleaving pMOX620 with XbaI and HindIII. A band was detected at a position of 4.2 kb in the host TK62 strain, while it was detected at a position of 7.3 kb in the gene-disrupted strain. After alcohol oxidase gene-disrupted strain was cultured in a YPD medium until it reached stationary phase, a strain lacking URA3 gene resistant to 5-fluoroorotidylic acid (5-FOA) was obtained according to a known method (Sakai Y. et al., J. Bacteriol., 174, 5988 (1992)).

Figure 10:
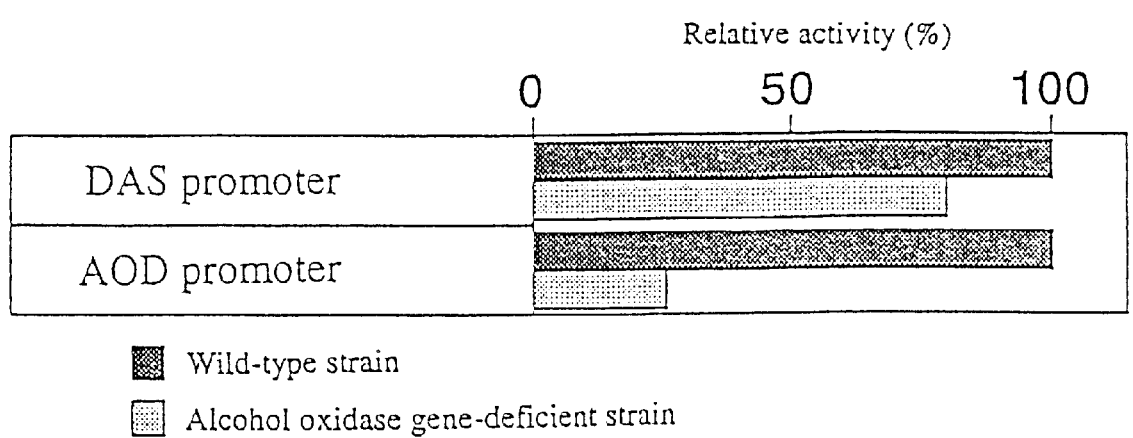
FIG. 10 shows activities of acid phosphatase of strains, which are obtained by transforming wile-type or alcohol oxidase gene disrupted strains with pDSPH1 or pAXPH1, after 24 hours of induction with methanol. The activity of acid phosphatase is defined as a relative value to the activity (as 100%) of the wild-type strain.

The resulting double mutant strain, which has mutations of both alcohol oxidase gene and URA3 gene, was transformed with plasmid pDSPH1 or pAXPH1, which was cleaved with BamHI. Strains integrated with one copy of the inserted plasmid were selected, and then the acid phosphatase activity 24 hours after induction by methanol was assayed according to the method as described above. As shown in FIG. 10, no significant difference in the activity among hosts was observed in expression by DAS promoter, but in expression by AOD promoter, significantly decreased activity was observed in the alcohol oxidase gene-deficient strain. Because this alcohol oxidase gene-deficient strain cannot metabolize methanol, induction may be carried out by methanol only. Therefore, these results suggest that induction of DAS promoter was mainly due to methanol and induction of AOD promoter was due to a metabolite(s) of methanol rather than methanol.

As described above, it was demonstrated that dihydroxyacetone synthase gene promoter is superior to alcohol oxidase gene promoter in that it is induced rapidly and strongly by methanol.

All publications, patents and patent applications cited herein are incorporated herein by reference in their entirety. The above-described examples are illustrative of the present invention, and the invention is not limited to them. It will be understood to a person skilled in the art that the present invention may include modification and variations without departing from the spirit and scope of the invention.

What is claimed is:

1. A promoter for dihydroxyacetone synthase gene from *Candida boidinii*, selected from the group consisting of a nucleotide sequence comprising the contiguous 498 bp of residues 364–861 of SEQ ID NO:1, and a sequence having at least 90% sequence homology to residues 364–861 of SEQ ID NO:1.

2. A promoter for dihydroxyacetone synthase gene from *Candida boidinii*, selected from the group consisting of a nucleotide sequence comprising the contiguous 861 bp of residues 1–861 of SEQ ID NO:1, and a sequence having at least 90% sequence homology to residues 1–861 of SEQ ID NO:1.

3. A promoter for dihydroxyacetone synthase gene from *Candida boidinii*, selected from the group consisting of nucleotide sequence comprising the contiguous 1,281 bp of residues 1–1,281 of SEQ ID NO:1, and a sequence having at least 90% sequence homology to residues 1–861 of SEQ ID NO:1.

4. A promoter for dihydroxyacetone synthase gene from *Candida boidinii*, selected from the group consisting of a nucleotide sequence comprising the contiguous 1,843 bp of residues 1–1,843 of SEQ ID NO:1, and a sequence having at least 90% sequence homology to residues 1–1,843 of SEQ ID NO:1.

5. An expression cassette, which comprises the promoter of any one of claims 1 to 4, and a heterologous gene.

6. The expression cassette of claim 5, which further comprises a terminator.

7. An expression vector which comprises the expression cassette of claim 5.

8. A cell transformed with the vector of claim 7.

9. A method for producing an expression product of a heterologous gene, which comprises culturing the cell of claim 8 in an appropriate medium and recovering the expression product of said heterologous gene from the cultured cell.

10. An expression vector which comprises the expression cassette of claim 6.

11. A cell transformed with the vector of claim 10.

12. A method for producing an expression product of a heterologous gene, which comprises culturing the cell of claim 11 in an appropriate medium and recovering the expression product of said heterologous gene from the cultured cell.

* * * * *

SEQUENCE LISTING

```
<160> NUMBER OF SEQ ID NOS: 23

<210> SEQ ID NO 1
<211> LENGTH: 1843
<212> TYPE: DNA
<213> ORGANISM: Candida boidinii

<400> SEQUENCE: 1
gaattcaaaa tgtggagaaa agaaatcagt tttctcttat tttaagacag gcatgatgct      60
gtgttattaa aaagatgtgt atatttgatt ggttcattaa aattttaaaa tatgactaag     120
ctaaatgata atttatgttt atttttccac tagatgctaa ttgtctagaa caaaaactaa     180
aaaaatcaat cttttcaatg tgtccgctat tccgctccaa tgaagtgatg attctgttcc     240
```

```
gtggaaagca gaataattaa aatgccaaca aagattaaga tatggctatt ttaggaatgc     300
agaaagtatg atcatgatga cagatttaac ctattgtctg ttatgtaatc ttttaaattt     360 tataatttt atttatttat ttcttgattc aattaatttt atctgactct tttctcttgg      420
aaaaatactc attgaggtga aattgtggag tcaattagcg gtcaacaaaa tgggaaacag     480
tttatgtgta ttttggtac gtacatatct gcaatcgtgc tgcttctgac gttttcaaaa     540
cataagaaat tttgaaattt tttttgcaat ataacaatga cacaatagcc attgtttgac    600
aaaatttatt aaaagcaacg taactaacct cttttaaaga tttgtaactt gtagccgacc    660
ttccagaact ctgacagtaa aatacgcttg gccgaacctc gcctgcgatt agtgatccgc    720
cagtaggtgc cagattttgc ggcttaccta atatttggtg gacctctcag ttgcatttca    780
gccgactgtc ctatgtggct gaatatcatt ttgcctgtcg gcttcttccc agaaatgtag    840
gctccctatt ccaaaaaggg aaatcggccg aatccgtttg ttcaacattt gtttccttgg    900
attagcgtag tcttcagtca agtggactgg atttcaaggg ataaactggg ctgaactggt    960
gcgtgcagga tatgaaaatg aatatgaata attggtaatt cagtcaacat ggctaaatcg   1020
gttctggatt attgcaaatg cttttcagag aattaaagtt ggtttggggg tattttcaat   1080
gtgtgagttt ataattccc actccgtgtt gttcccctta cagtactaca aaatttgcat    1140
agctttcagc atacggtgga tattatttc acctatgata taggaaacca taataatagt    1200
aatacgttaa agttcatttt attgagacta cgcaaatttt accgtctcat aattcaataa    1260
ctaaatccga atggtcaatc gaaatttaaa cttagtttgg atagtttctt attcttatcc    1320
cctctttgcg ctaacagatt gttttttttct tttgcaatta ttttttttata tcattttca    1380 gttttaacca ttaaccccc tattaattaa aagataatta tacttacctt attatttgaa    1440
aaattaaccc catatttaat caattagcca ttttaatttc ttttttttaat gttatcgtct    1500 aaattctcat cctgtaggtt aatttatat ttcttattat ttttgtttta tcttttgccg    1560
acgacccttt tttacttttt ttttataggc aaataattaa atgtaggttc atttaacatt   1620 tttcttttt ttctgaaagt atataagaaa tttaaaatca ccaatttta ttttaaattt      1680 atttattcat tttattttta tttctatcta tctatctatc tttaaatatc attattaaat    1740
tataagaata attaatttt atttgttcat ataatttat aagagaaaaa acaactttag      1800
agaaaaacaa aaagataata aattattaaa aaaaattaca aaa                       1843
```

<210> SEQ ID NO 2
<211> LENGTH: 13
<212> TYPE: PRT
<213> ORGANISM: Candida boidinii

<400> SEQUENCE: 2

Met Ala Leu Ala Lys Ala Ala Ser Ile Asn Asp Asp Ile
1               5                   10

<210> SEQ ID NO 3
<211> LENGTH: 39
<212> TYPE: DNA
<213> ORGANISM: Candida boidinii

<400> SEQUENCE: 3
atggctctcg caaaagctgc ttcaattaac gatgatatc                            39

<210> SEQ ID NO 4
<211> LENGTH: 36

```
<212> TYPE: DNA
<213> ORGANISM: Artificial Sequence
<220> FEATURE:
<223> OTHER INFORMATION: Description of Artificial Sequence: Primer

<400> SEQUENCE: 4
gggctcgagg aattcaaaat gtggagaaaa gaaatc                        36

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 5
cccgcggccg cttttgtaat tttttttaat aatttattat cttttgttt ttc      53

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cctcttttaa agaattctaa cttgtagccg acc                           33

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcttcttccc agaattctag gctccctatt ccaaaaagg                     39

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggggaattct aaatccgaat ggtcaatcg                                29

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggggaattcg aaatttaaac ttagtttgga tag                           33

<210> SEQ ID NO 10
<211> LENGTH: 33
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 10
ggggaattca tagtttctta ttcttatccc ctc                           33

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggagatctt tttttatatc atttttcagt tttaaccatt aac                43

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggagatctt attgaattat gagacggtaa aatttgc                       37

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggagatctt ccaccgtatg ctgaaagcta tgcaaatttt g                  41

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggagatcta actttaattc tctgaaaagc atttgcaata atc                43

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggagatcta ccagttcagc ccagtttatc ccttgaaatc                    40

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
gggagatctc cctttttgga atagggagcc tacatttc                                    38

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggagatctc accaaatatt aggtaagccg caaaatctg                                   39

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gggagatctg gtcggctaca agttacaaat ctttaaaaga g                                41

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gggagatcta aatttcaaaa tttcttatgt tttgaaaacg tcag                             44

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gggagatctc gctaattgac tccacaattt cacctcaatg                                  40

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccagatcttg ataataaggt atactacatt ttatc                                       35

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 22
caatgagccg ttgaattgac gagtg                                          25

<210> SEQ ID NO 23
<211> LENGTH: 21
<212> TYPE: PRT
<213> ORGANISM: Candida boidinii

<400> SEQUENCE: 23

Met Ala Leu Ala Lys Ala Ala Ser Ile Asn Asp Asp Ile His Asp Leu
 1               5                  10                  15

Thr Met Arg Ala Phe
            20
```